(12) United States Patent
Dirk

(10) Patent No.: US 8,570,498 B2
(45) Date of Patent: Oct. 29, 2013

(54) FILTERS, ILLUMINANTS, AND CUSTOMIZED SPECTRAL PROFILES FOR REDUCING PERCEPTIBLE CHANGES IN APPEARANCE

(75) Inventor: Carl W. Dirk, El Paso, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 524 days.

(21) Appl. No.: 12/780,546

(22) Filed: May 14, 2010

(65) Prior Publication Data

US 2010/0290231 A1 Nov. 18, 2010

Related U.S. Application Data

(60) Provisional application No. 61/178,585, filed on May 15, 2009.

(51) Int. Cl.
*G01N 1/00* (2006.01)
*G01J 3/40* (2006.01)

(52) U.S. Cl.
USPC ............ 356/72; 356/303; 356/300; 362/231

(58) Field of Classification Search
USPC ............... 356/72, 73, 303; 362/231; 382/312
See application file for complete search history.

(56) References Cited

U.S. PATENT DOCUMENTS

| | | | |
|---|---|---|---|
| 5,173,808 A | 12/1992 | Auer et al. ............... 359/722 |
| 5,267,061 A | 11/1993 | Ansley et al. ............. 359/15 |
| 5,786,591 A | 7/1998 | Asahi ....................... 250/226 |
| 6,031,653 A | 2/2000 | Wang ........................ 359/247 |
| 6,075,872 A | 6/2000 | McGuire .................. 382/100 |
| 6,097,856 A * | 8/2000 | Hammond, Jr. ......... 382/312 |
| 6,154,708 A | 11/2000 | Koashi ....................... 702/40 |
| 7,387,405 B2 | 6/2008 | Ducharme et al. ...... 362/231 |
| 7,548,341 B2 * | 6/2009 | Gotoh et al. .............. 358/1.9 |
| 7,626,693 B1 | 12/2009 | Dirk ......................... 356/300 |
| 7,663,739 B2 | 2/2010 | Dirk ............................ 356/72 |
| 2002/0012461 A1 | 1/2002 | MacKinnon et al. .... 382/164 |
| 2004/0105261 A1 | 6/2004 | Ducharme et al. ...... 362/231 |
| 2004/0125607 A1 | 7/2004 | Dirk ......................... 362/458 |
| 2010/0085563 A1 | 4/2010 | Dirk ......................... 356/300 |
| 2010/0165337 A1 | 7/2010 | Dirk ......................... 356/303 |

FOREIGN PATENT DOCUMENTS

| | | |
|---|---|---|
| EP | 1 122 588 | 8/2001 |
| WO | WO 92/01557 | 2/1992 |
| WO | WO 94/14089 | 6/1994 |
| WO | WO 96/10211 | 4/1996 |
| WO | WO 01/36864 | 5/2001 |
| WO | WO 01/46617 | 6/2001 |
| WO | WO 02/063206 | 8/2002 |
| WO | WO 2004/036161 | 4/2004 |

OTHER PUBLICATIONS

Office Communication issued in U.S. Appl. No. 10/688,200, mail date Aug. 29, 2008.

(Continued)

*Primary Examiner* — Layla Lauchman

(57) ABSTRACT

Customized spectral profiles, and filters and illuminants having a customized spectral profile, optimized to reduce light in one or more wavelength regions for which one or more pigments are relatively more susceptible to perceptible changes in appearance.

18 Claims, 6 Drawing Sheets

(56) References Cited

OTHER PUBLICATIONS

Office Communication issued in U.S. Appl. No. 10/688,200, mail date Mar. 5, 2009.

Office Communication issued in U.S. Appl. No. 11/232,442, mail date May 15, 2008.

Office Communication issued in U.S. Appl. No. 12/648,714 mail date Jun. 24, 2010.

Piegari, "Ultraviolet, visible and infrared performance of coated glass for museums," *Optical and Infrared Thin Films*, 4094:74-82, 2000.

U.S. Appl. No. 12/466,589, "Protective Light Filters and Illuminants Having Customized Spectral Profiles," by Carl W. Dirk, filed May 15, 2009.

Weintraub, "The color white: is there a 'preferred' color temperature for the exhibition of works of art?" *WAAC Newsletter*, 21:1-6, 2000.

\* cited by examiner

FILTERS, ILLUMINANTS, AND CUSTOMIZED SPECTRAL PROFILES FOR REDUCING PERCEPTIBLE CHANGES IN APPEARANCE

RELATED APPLICATIONS

This application claims priority to U.S. Provisional Application No. 61/178,585, filed May 15, 2009, which is incorporated by reference in its entirety.

BACKGROUND

1. Field of the Invention

The present invention relates generally to optics, spectroscopy, and illumination sources. More particularly, but not by way of limitation, the present invention relates to customized spectral profiles and filters and illuminants having customized spectral profiles. Representative embodiments relate to customized spectral profiles that, when incorporated into a filter or illuminant (e.g., a filter or illuminant having the customized spectral profile), may be used for (a) protecting works of art or other objects that may be susceptible to perceptible changes in color, and/or (b) aesthetically rendering objects.

2. Background Information

It is known that the quality of light falling upon a work of art affects the degree to which that work of art will be damaged through photochemical processes. Photodamage of works of art, in turn, is an important concern not only for the financial well-being of museums, but also for the preservation of this and foreign cultures.

One of the most common methods to minimize photodamage is to minimize the amount of ultraviolet and/or infrared radiation that impacts artwork. Although this method may be somewhat effective, it unfortunately does not prevent damage to the artwork imposed by photons that do not significantly affect the color rendering of that artwork. In other words, today's solutions do not block visible-light photons that do not contribute to the visualization of the object. Put yet another way, today's solutions are not equipped to render only the necessary portions of photometric light—transmit visible-light photons that significantly affect the visualization of a particular object (e.g., light necessary for proper color rendering) while blocking photons unneeded for this task.

It is also known that the quality of light falling upon a work of art affects the aesthetics or color rendering of that art. For instance, illumination by fluorescent lighting may give a work of art a different "look and feel" than when the art is illuminated by incandescent lighting. While the underlying physical reasons for this difference are relatively complex, existing filters and illuminants may be ill-equipped to aesthetically render an object while simultaneously protecting the object. In particular, existing filters and illuminants are generally not equipped to simultaneously render and protect an object such as a piece of art as well as may be achieved. Accordingly, many times, if a piece of art is well-protected, museum patrons cannot fully appreciate the colors of the artwork, such as, for example, the way in which the artist himself or herself saw a particular work of art as it was being painted. Conversely, if a piece of art is illuminated such that the colors are more fully rendered, the artwork may not be as well protected as it could be such that the piece of art may be subject to photochemical damage at a faster rate than is otherwise desired.

These issues with today's technology are not meant to constitute an exhaustive list nor to limit the applications or features in this disclosure. Rather, they illustrate by example a need for the customized spectral profiles, filters, and illuminants of this disclosure.

SUMMARY

The present disclosure includes various embodiments of methods, customized spectral profiles, and filters and illuminants having customized spectral profiles that are configured or optimized to protect pigments from perceptible changes in appearance (e.g., changes in color), such as, for example, without regard for photochemical damage that may result in non-perceptible or less-perceptible changes in appearance.

Some embodiments of the present methods of generating a customized spectral profile comprise: determining for one or more pigments one or more wavelength regions for which the one or more pigments are relatively more susceptible to perceptible changes in color than for one or more other less-susceptible wavelength regions; and optimizing a spectral profile to generate a customized spectral profile such that an illuminant or filter configured to have the customized spectral profile will reduce light in the one or more more-susceptible wavelength regions.

In some embodiments of the present methods, optimizing further includes optimizing the spectral profile to generate a customized spectral profile such that an illuminant or filter configured to have the customized spectral profile will reduce light to a lesser degree in the less-susceptible wavelength regions than in the one or more more-susceptible wavelength regions. In some embodiments, at least one less-susceptible wavelength region is more susceptible to photochemical damage than at least one more-susceptible wavelength region.

In some embodiments of the present methods, the step of optimizing further comprises optimizing the custom spectral profile such that an illuminant or filter configured to have the customized spectral profile will also have a color rendering index (CRI) of at least 85 for the one or more pigments relative to an unfiltered reference illuminant. In some embodiments, the step of optimizing further comprises optimizing the custom spectral profile such that an illuminant or filter configured to have the customized spectral profile will also have a color rendering index (CRI) of at least 90 for the one or more pigments relative to an unfiltered reference illuminant. In some embodiments, the step of optimizing further comprises optimizing the custom spectral profile such that that an illuminant or filter configured to have the customized spectral profile will also have a color rendering index (CRI) of at least 95 for the one or more pigments relative to an unfiltered reference illuminant. In some embodiments, the unfiltered reference illuminant is an incandescent lamp having a color temperature of about 3000K.

In some embodiments of the present methods, the step of determining comprises: obtaining a reflection spectrum for the one or more pigments; and determining color change susceptibility (CCS) of the one or more pigments across the reflection spectrum. In some embodiments, the step of optimizing comprises: identifying one or more peaks or shoulders of CCS across the reflection spectrum for the one or more pigments, the peaks or shoulders each corresponding to a wavelength region in which the pigment is relatively more susceptible to damage causing perceptible changes in appearance; and modifying the customized spectral profile to reduce light in the one or more wavelength regions. In some embodiments, the step of determining CCS comprises calculating a color change or change in color rendering per unit change in reflectance across the reflection spectrum for the pigment. In some embodiments, the step of obtaining a reflection spectrum comprises imaging the reflection spectrum with a spectral imaging camera or other spectral imaging device controlled by suitably programmed software.

In some embodiments of the present methods, the step of determining comprises determining two or more wavelength regions in which the one or more pigments is relatively more susceptible to damage causing perceptible changes in appearance, and where modifying comprises modifying the customized spectral profile to reduce light in each of the two or more wavelength regions. Some embodiments comprise coupling one or more filter layers to a substrate such that the substrate and filter layers are configured to have the customized spectral profile. Some embodiments comprise coupling one or more filter layers to an illuminant such that, if the illuminant is energized, the filter layers are configured to filter light from the illuminant according to the customized spectral profile.

Some embodiments of the present methods of generating a customized spectral profile, comprise: determining for an image a plurality of wavelength regions in which one or more pigments of the image are relatively more susceptible to damage causing perceptible changes in appearance; optimizing a custom spectral profile to reduce light in each of the wavelength regions.

Some embodiments of the present apparatuses comprise: an illuminant configured to emit light if the illuminant is energized; a plurality of filter layers coupled to the illuminant; where the apparatus is configured such that, if the illuminant is energized and emits light, the filter layers will: (a) block a portion of the light having wavelengths in one or more selected wavelength regions in which one or more pigments are relatively more susceptible to damage causing perceptible changes in appearance, and (b) transmit a portion of the light such that the transmitted light has a color rendering index of at least 85 for the one or more pigments relative to the illuminant without filter layers. In some embodiments, the filter layers are physically coupled to the illuminant. In some embodiments, one or more of the filter layers are in direct contact with the illuminant.

Any embodiment of any of the present methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE
EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a filter that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps. For example, in a method that comprises identifying and optimizing, the method includes the specified steps but is not limited to having only those steps. For example, such a method could also include coupling.

Further, a device or structure (e.g., a customized spectral profile, filter, illuminant, etc.) that is configured in a certain way is configured in at least that way, but it can also be configured in other ways than those specifically described.

This application incorporates by reference each of: (1) U.S. patent application Ser. No. 10/688,200 entitled "Customizable Spectral Profiles for Filtering," by Carl W. Dirk, which was filed on Oct. 17, 2003; and (2) U.S. patent application Ser. No. 11/232,442 entitled "Illumination Sources and Customizable Spectral Profiles," by Carl W. Dirk, which was filed on Sep. 21, 2005.

Figure 1:
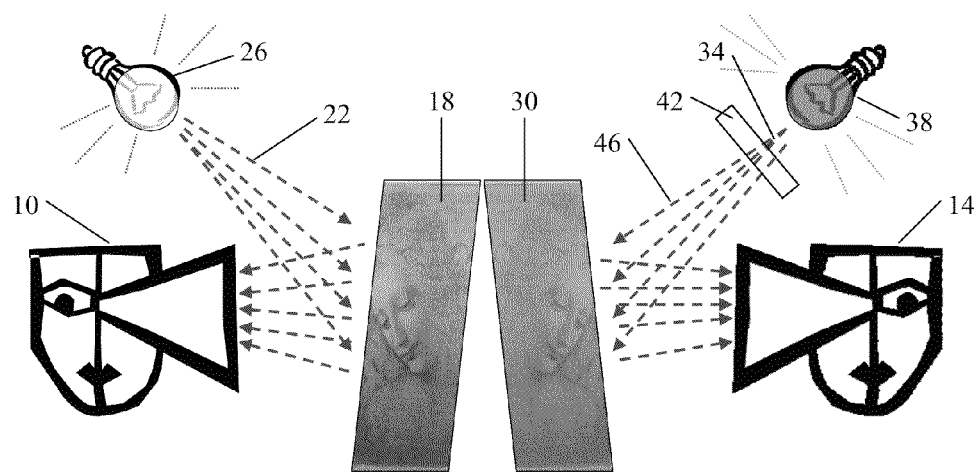
FIG. 1 depicts an unfiltered illuminant and a filtered illuminant.

Referring now to the drawings, and more particularly to FIG. 1, shown therein for introduction is a first person 10 and a second person 14. First person 10 is shown viewing a first object 18 (e.g., a piece of artwork) by the light 22 of a first source illuminant 26. Second person 14 is shown viewing a second object 30 by the light 34 of a second source illuminant 38 that has passed through a filter 42 (i.e., second object 30 is illuminated by filtered light 46. Although first source illuminant 26 may illuminate first object 18 sufficiently for viewing, it may also provide an excess of light or photons that may damage object 18. As such, filter 42 is configured to have a customized spectral profile that filters out or substantially blocks at least a portion of light 34 from second source illuminant 38. Although filter 42 is shown separate from second source illuminant 38, it should be understood that a filter (e.g., filter 42) can be coupled to or integral to an illuminant (e.g., second illuminant 38). For example, one or more filter layers can be coupled to a source illuminant (e.g., one or more of 3 LEDs can each be coated with one or more filter layers such that the combination of LEDs and/or filter layers are together configured to emit light having a customized spectral profile).

Through methods such as, for example, the methods described in the Dirk patent applications incorporated by reference above, customized spectral profiles can be generated or developed to have desirable illumination characteristics. Such customized spectral profiles can, for example, be incorporated into a filter (e.g., a filter can be formed or configured to have a customized spectral profile that is about equal to or substantially similar to the customized spectral profile), or be incorporated into an illuminant (e.g., an illuminant can be formed or configured to have a customized spectral profile that is about equal to or substantially similar to the customized spectral profile, e.g., by way of multiple illuminants, one or more filter layers, or the like).

Where a customized spectral profile is generated or optimized, and a filter or illuminant is configured to have a customized spectral profile is configured such that light transmitted through the filter will have a spectral profile substantially similar to the customized spectral profile that is generated or optimized. For example, a filter having the customized spectral profile will filter light from an illuminant (e.g., a source illuminant) which may be, for example, a specific illuminant such as a Sylvania 58533 lamp, a group of illuminants such as incandescent illuminants having a color temperature of about 3000K, one or more LEDs, one or more candles, and/or any other suitable illuminant. By way of another example, an illuminant configured to have a customized spectral profile (e.g., a filtered illuminant) is configured such that light emitted from the illuminant will have a spectral profile substantially similar to the generated or optimized customized spectral profile (e.g., when the generated or optimized customized spectral profile is defined in terms of percent (%) transmission, the illuminant's spectral profile may be determined or defined relative to an unfiltered illuminant or an illuminant that is not configured to have the customized spectral profile). By way of yet another example, when an illuminant and a filter are configured to have a customized spectral profile, one or both of the illuminant and filter can be configured such that when the illuminant is energized to emit light and that light is filtered through the filter, the filtered light will have a spectral profile substantially similar to the generated or optimized customized spectral profile (e.g., relative to an unfiltered illuminant or illuminant that is not so configured).

A number of references, factors, and characteristics of illumination and/or spectra may be useful for characterizing the customized spectral profiles, filters, and/or illuminants of the present disclosure. "Reference illuminants" can include established theoretical references (e.g., standard A illuminant, standard D65 illuminant, standard F7 illuminant), and/or one or more actual illuminants (e.g., incandescent or fluorescent illuminants, such as are manufactured or distributed by Sylvania throughout the United States). As will be understood by those of ordinary skill in the art standards A, D65, and F7 are well known theoretical reference illumination spectra, with: standard A representing an incandescent illuminant with a color temperature of 3000K; standard D65 representing daylight, and standard F7 representing a fluorescent illuminant with a broad-band daylight-imitating spectrum.

"Luminosity" or "luminous intensity" refers to perceived brightness of illumination. Luminosity can, for example, be calculated using (1) the Standard Vision Theory model in which luminosity is determined from luminance (Y), which is itself derived from the Photopic function; (2) the Helmholtz-Kohlrausch model in which luminosity may be determined from luminance (Y) and chromaticity (x,y); and/or (3) the opponent color theory in which luminosity may be determined from L*a*b* coordinates.

"Radiant power ratio" refers to the illumination per unit of power (lumens divided by watts of power) for an illuminant relative to a reference illuminant (e.g., Standard A incandescent illuminant). For example, where Standard A is the reference illuminant, Standard D65 has a radiant power ratio of about 1.27, and Standard F7 has a radiant power ratio of about 1.63. Since excess power may be more likely to increase photochemical damage, it may be desirable in some instances to reduce transmitted power. However, in order to reduce power while maintaining suitable illumination, it may be desirable in such instances to have a relatively high radiant power ratio. "Lumens/watt efficiency" is used in this disclosure as a percentage value based on the radiant power ratio of an illuminant. For example, where Standard A is the reference illuminant, Standard D65 has a lumens/watt efficiency of about 127%, and Standard F7 has a lumens/watt efficiency of about 163%.

"Color Difference" refers to a just-perceptible difference in color, i.e.: $\Delta E = DE = 1$. Color difference can be determined using: (1) the pre-L*a*b* color difference formula which is based on UVW in the 106-CIE Yuv coordinate system Pre-Lab Color Difference is UVW in the 106-CIE Yuv coordinate system; (2) the DE76 color difference formula; (3) the DE94 color difference formula, and/or the DE00 color difference formula.

"Adaptation" refers to the ability and tendency of the human brain to adapt to become adapted to a first color or color scheme such that when a second color or color scheme is introduced, the second color or color scheme is perceived differently than it may have been without the preceding color or color scheme. Adaptation can be determined or approximated (e.g., for color rendering models or determinations, as described in more detail below) using: (1) the von Kries model, which is used in the CIE-recommended color-rendering method of CIE 13.3; (2) the Bradford model, which may be used by Adobe Photoshop; and/or (3) the Nayatani Model given by CIE 109.2. The Nayatani model may be especially useful, accurate, and/or advantageous for widely different spectral distributions, differing color temperatures, and/or differing luminosities.

Color rendering refers to the accuracy with which colors are rendered by one illuminant relative to a reference illuminant. Color Rendering Index (CRI) is an indication of how well the illuminant is matched to the reference illuminant, with a CRI≡100 being a perfect match of the illuminant to the reference illuminant. For example, in FIG. 1, the CRI of the second source illuminant 38 and filter 42 could be calculated relative to the unfiltered illuminant 26 (which would act as the reference illuminant), or could be calculated relative to a theoretical reference illuminant (e.g., Standard A). CRI relates to color difference such that 4.6 CRI units are about equivalent to DE=1 color difference unit. In this way, just-perceptible changes in CRI occur between the following points: 100, 95.4, 90.8, 86.2, 81.6, and so on (even below zero in some instances). CRI can be determined by calculating color difference between the illuminant and the reference illuminant and applying adaptation models to determine the appropriate perceived CRI. CRI can be determined using CIE 13.3, which generally uses reflection spectra for 8 colors in the Munsell 8 color reference. Other reflection spectra can also be used, including, for example, reflection spectra obtained for individual pigments, for mixtures of pigments, for individual objects (e.g., paintings or works of art), for portions of individual objects, for groups of objects (e.g., representative samples of impressionist paintings, oil paintings, watercolor paintings, charcoal drawings), or any other useful reflection spectra.

Aspects of the present disclosure relate to optimization of customized spectral profiles to reduce perceptible changes in appearance of an object (such as a piece of artwork, pigment, or the like) which may, for example, include changes in appearance. Such changes in appearance may be considered in context with the at-least-partially related concepts of hole burning, damage spectrum profiles, and color change susceptibility (CCS).

Figure 2:
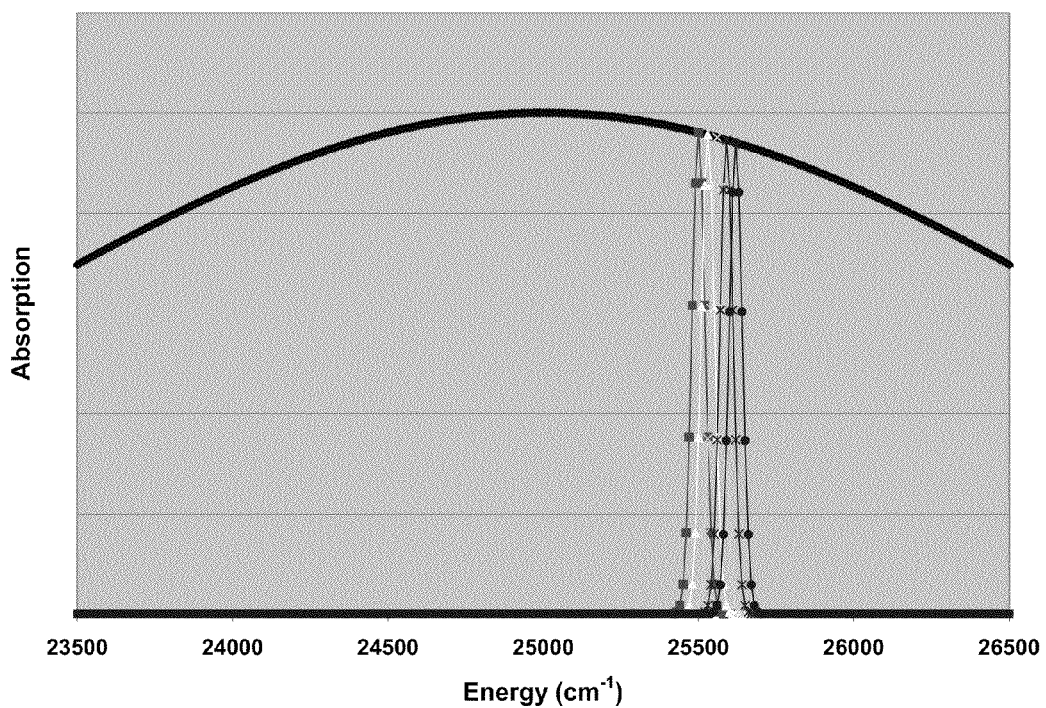
FIG. 2 depicts an arbitrary example of an absorption spectrum for a solid material.

The concept of hole burning depends on the consideration that within a solid material (such as a pigment, substrate having a pigment thereon or therein, paint, ink, or the like), molecules are trapped in local environments and orientations such that they are energetically different or interact with light in different (e.g., enhanced or reduced) ways depending, for example, on the polarization of light. The energetic differences may mean that, within a distribution of molecules in a solid material, some may absorb light at longer wavelengths and some may absorb light at shorter wavelengths. As such, a broad absorption or reflection feature within a spectrum typically consists of many smaller absorption ensembles which each share the same energy. FIG. 2 partially illustrates this concept in an absorption spectrum profile for an arbitrary solid material. Specifically, as illustrated by the peaks in the energy region between about 25000 cm$^{-1}$ and about 26000 cm$^{-1}$, individual absorption ensembles cooperate to define the broader absorption spectrum profiles across the entire range of energies.

Figure 3:
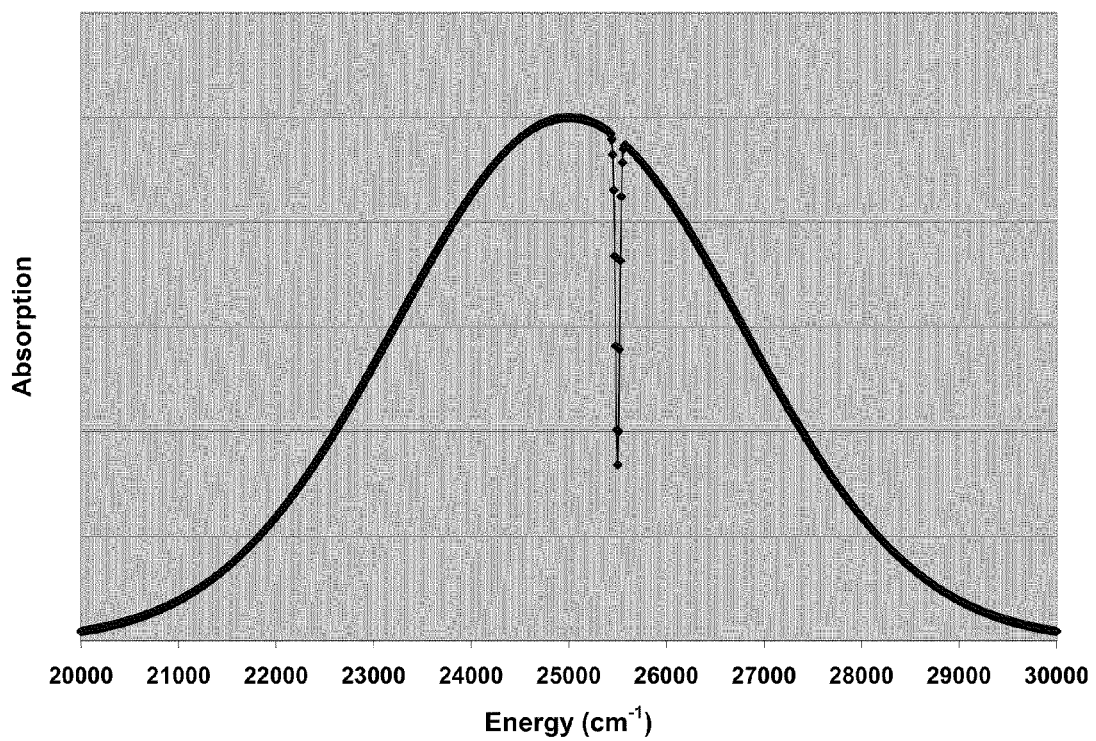
FIG. 3 depicts an arbitrary example of an absorption spectrum that has suffered damage from hole burning.

Since, in solid materials, molecules are typically locked in their energetic and orientational positions, excess irradiation at a wavelength or wavelength region (e.g., by a laser) can cause photochemical damage to a selected ensemble and deplete it, such that the absorption spectrum profile is damaged or changed, as illustrated by the relatively sharp minimum between about 25000 cm$^{-1}$ and about 26000 cm$^{-1}$ in FIG. 3. Since the molecule is a solid and all other molecules and ensembles are fixed, molecules from another ensemble that is energetically different cannot generally fill in the gap created in the spectrum. The gap in the spectrum is what is referred to as a "hole", and the process of creating the hole is called "hole burning". While FIG. 3 illustrates the effect of a narrow laser, such damage can also be caused by a broader beam, and can leave a broader hole. For an illuminant having a spectral distribution with peaks, the peaks of the illuminant can selectively deplete the corresponding spectral regions of an object (e.g., pigment or painting with multiple pigments) that is being illuminated. This could lead to broader holes (damaged wavelength regions).

Damage spectrum profiles (or "damage profile spectra") are the consequence of selectively irradiating in narrow wavelength bandwidths and determining how this changes the reflection spectrum of a material. This may be closely related to the concept of hole burning. In principle, irradiating in a particular wavelength region should only cause spectral changes in that region, as discussed above for hole burning. Actual damage, however, may be more complex. Real-world materials rarely consist of only one type of molecule that can be affected by light. Thus, a real material may consist of a number of materials (e.g., pigments) each with different sensitivities to light, as well different wavelength regions which may be more sensitive than others. These wavelength ranges may incompletely overlap so that spectral hole burning depletes some wavelength regions more aggressively than others. In addition, the width of the more-sensitive wavelength regions may vary. Thus, in FIG. 2 where many narrow peaks contribute to a broad peak, the lifetime of the excitation can affect the breadth of these more narrow peaks.

The breadth of such peaks may be due to 'uncertainty' broadening, such as may be understood with reference to the Heisenberg Uncertainty Theory. Different molecules often possess different uncertainty broadening. For a mixture of molecules in a real-world material, the different light and spectral sensitivities, different broad absorptions which may incompletely overlap, and different uncertainty broadenings can mean that irradiation in one wavelength region can sometimes cause changes in wavelength regions which are not being irradiated, or larger-than-expected changes in other wavelength regions which are being irradiated. Thus, the effects of hole burning can be broader than and/or remote from the wavelength region that receives light. As a result, there can be considerable complexity to spectral hole burning, and the color change from irradiation in narrow band regions cannot necessarily be fully predicted with reference to a single wavelength of light. As such, in some embodiments of the present methods, it may be beneficial to irradiate an object and experimentally obtain damage spectrum profiles (e.g., one or more reflection spectrum profiles before and/or after irradiation).

Certain embodiments of the present methods of generating a customized spectral profile comprise: determining for one or more pigments (e.g., two or more, a plurality, etc.) one or more wavelength regions for which the one or more pigments are relatively more susceptible to perceptible changes in color than for one or more other less-susceptible wavelength regions; and optimizing a spectral profile to generate a customized spectral profile such that an illuminant or filter configured to have the customized spectral profile will reduce light in the one or more (e.g., two or more, a plurality, etc.) more-susceptible wavelength regions. For example, when a reflection spectrum changes due to photochemical damage, this can cause a change in color. We define a quantity called Color Change Susceptibility (CCS) which is the color change or color difference ($\Delta E$ or DE) for a given change in reflection ($\Delta R$). Since the reflection has a wavelength dependence, the CCS must have a wavelength dependence and is more accurately defined as $\Delta R[\lambda]$. CCS can be defined by Equation 1:

$$CCS(\lambda) \equiv \Delta E/\Delta R(\lambda), \lim[\Delta R(\lambda) \to 0] \qquad (1)$$

In practice, it may be sufficient to calculate CCS using differences of 1% in reflectance. This can be determined by systematically and sequentially stepping through a reflection spectrum, changing the value at a wavelength segment by 1%, and then calculating the color difference one would expect between the initial spectrum and the 1%-change spectrum, as is shown in FIG. 4 for Windsor & Newton's Flame Red Gauche (FRG) pigment.

Figure 4:
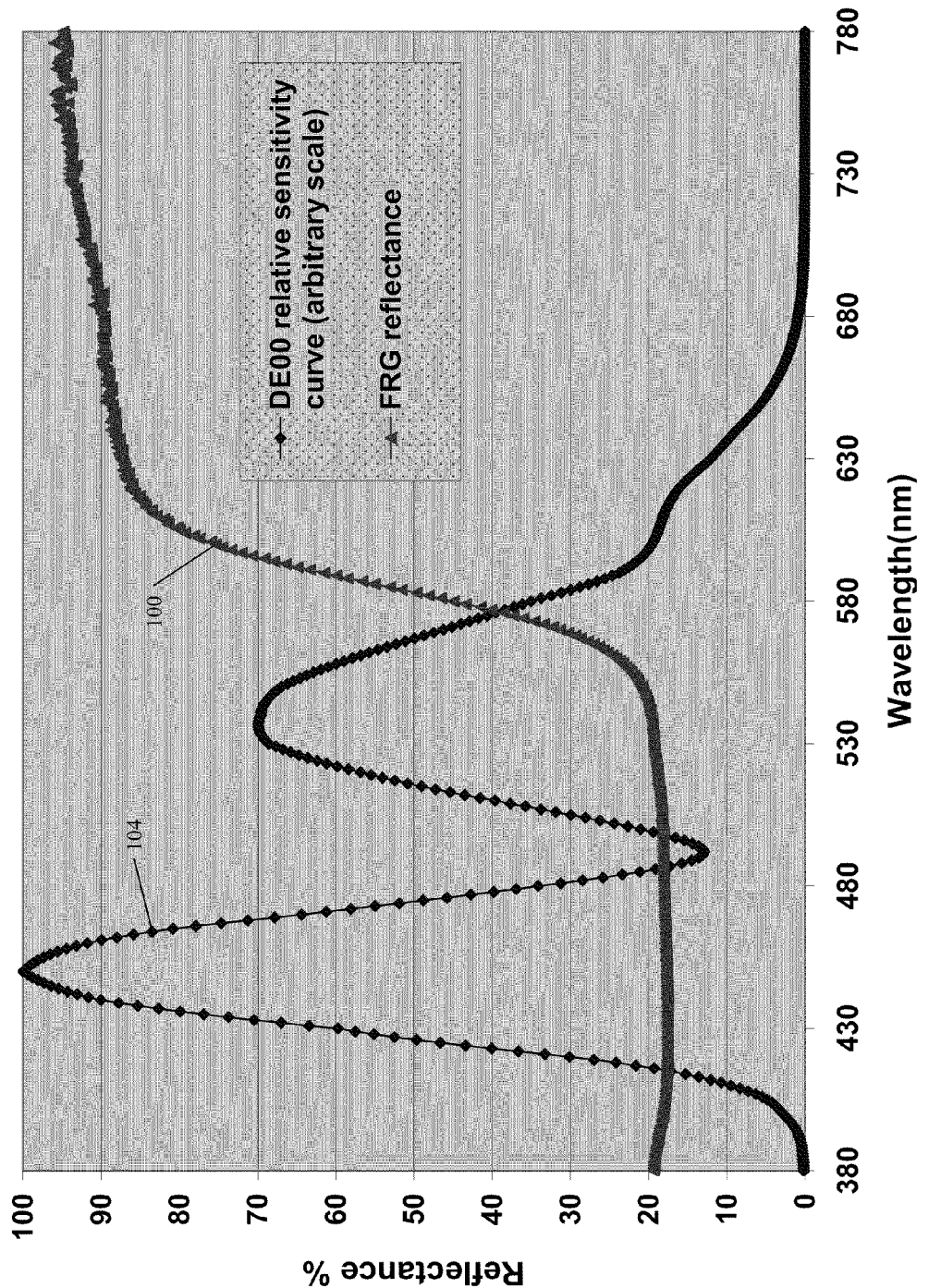
FIG. 4 depicts color change susceptibility (CCS) of Windsor & Newton's Flame Red Gauche pigment.

Accordingly, in certain embodiments of the present methods, such as the one illustrated in FIG. 4, the step of determining comprises: obtaining a reflection spectrum (e.g., 100) for the one or more pigments (e.g., flame red gauche); and determining color change susceptibility (CCS) (e.g., 104) of the one or more pigments across the reflection spectrum. In some embodiments, the step of optimizing comprises: identifying one or more peaks or shoulders of CCS across the reflection spectrum for the one or more pigments, the peaks or shoulders each corresponding to a wavelength region in which the pigment is relatively more susceptible to damage causing perceptible changes in appearance; and modifying the customized spectral profile to reduce light in the one or more wavelength regions. In some of these embodiments, the step of determining CCS comprises calculating a color change or change in color rendering per unit change in reflectance across the reflection spectrum for the pigment.

For example, FIG. 4 illustrates an FRG reflectance spectrum 100, and the expected color change (difference) 104 for the FRG pigment calculated using the DE00 (CIE 2000) color-difference formula. The units for spectrum 104 are color change per unit change in reflection, and the scale is not shown in this example. One can use any color difference equation to calculate CCS (e.g., DE76, etc.), though DE00 is used here because it is presumably more accurate. The CCS shown here has three peaks or shoulders, and in general, CCS spectra may include similar features in similar locations for most pigments. Typically, peaks are larger for blue than most other pigments, and this explains why blue may be the most difficult color to match when trying to find a pigment to match in another object. Of particular relevance for optimizing the color rendering of a customized spectral profile, the three peaks or shoulders roughly correspond to wavelength regions near the peaks of the cone sensitivities of human eyes. As shown, for a 1% change in reflectance, the perceptible color change (DE00) curve includes a peak at about 450 nanometers (nm) and a peak at about 535 nm. As such, it can be expected that changes in reflectance at or near these peaks will result in larger perceptible changes in color of the pigment (e.g., that the FRG pigment is relatively more susceptible to perceptible changes in color for the wavelength regions surrounding about 450 nm and about 535 nm).

CCS generally illustrates, spectrally, where the maximum color change can be expected to occur for a change in reflection in a given spectral region. Thus, hole burning in some spectral regions can produce a larger color change than in other spectral regions. A damage profile spectrum that is expressed in color change (instead of reflection change) as a function of wavelength is actually a convolution of the actual reflection change with CCS. CCS can predict what spectral regions of a material are most susceptible to producing color change if hole burning occurs in those regions. It can be a useful predictive tool of where one might not want excessive light in certain spectral regions, in order limit color change. Because some materials are complex mixtures, in which spectral changes can occur remote from the region that is irradiated, it may not always predict exactly for all materials, but can be used as tool to guide the development of illumination that minimizes perceptible changes in appearance of an illuminated object.

Note also that since CCS is nonlinearly related to the actual change in reflection, it shows that chemical change and color change are generally not linearly related. This revelation suggests that while large photochemical changes may occur, CCS can help predict and optimize spectral profiles which should minimize changes in appearance. The present CCS methods, filters, and illuminants depart from traditional methods and filters that protect artwork from photochemical changes without reference to specific changes in appearance, and comprise a novel, second approach that can be targeted to minimize changes in appearance, in some cases, without reference to the magnitude of photochemical damage. In essence, CCS represents a new tool for preserving works of art and/or archival documents. In many instances, it may be beneficial to slow changes in appearance rather than reducing photochemistry alone.

In certain embodiments of the present methods, the step of obtaining a reflection spectrum comprises imaging the reflection spectrum with a spectral imaging camera or other spectral imaging device controlled by suitably programmed software. In other embodiments, reflection spectra can be obtained in any suitable fashion, including, for example, obtaining a known reflection spectrum for a known pigment, imaging one or more reflection spectra for one or more pigments (e.g., a plurality of pigments in a painting, and/or from any other suitable source).

In this way, a customized spectral profile can be optimized to reduce light in these one or more more-susceptible wavelength regions. For example, a customized spectral profile can be optimized such that a filter or illuminant having the customized spectral profile will reduce light between about 440 nm and about 460 nm and/or between about 525 nm and about 545 nm. By way of yet another example, a customized spectral profile can be configured to reduce light within any range of a peak in the color change curve for any pigment, including, for example, ±100 nm, ±90 nm, ±80 nm, ±70 nm, ±60 nm, ±50 nm, ±40 nm, ±30 nm, ±20 nm, ±10 nm, ±5 nm, ±4 nm, ±3 nm, ±2 nm, ±1 nm, or any other range (e.g., +5 nm and −10 nm).

In some embodiments, optimizing further includes optimizing the spectral profile to generate a customized spectral profile such that an illuminant or filter configured to have the customized spectral profile will reduce light to a lesser degree (e.g., up to and including not reducing light at all) in the less-susceptible wavelength regions than in the one or more more-susceptible wavelength regions. For example, there may be a lesser need to reduce light in less-susceptible wavelength regions (wavelength regions that are less susceptible to perceptible color changes) such that there is less need to reduce light in those less-susceptible wavelength regions, even if those less-susceptible wavelength regions will sustain relatively more, but less-perceptible, photochemical damage. For example, the color change curve includes relative minima at about 380 nm and about 485 nm. In wavelength regions around these minima, light may not be reduced at all. Since the focus of the present methods is on minimizing perceptible changes in appearance, in some embodiments, at least one less-susceptible wavelength region can be more susceptible to photochemical damage than at least one more-susceptible wavelength region, and even so, a customized spectral profile may be optimized to only reduce light in one or more more-susceptible (to perceptible color changes) without reducing or otherwise affecting light in the less-susceptible wavelength regions.

Figure 5:
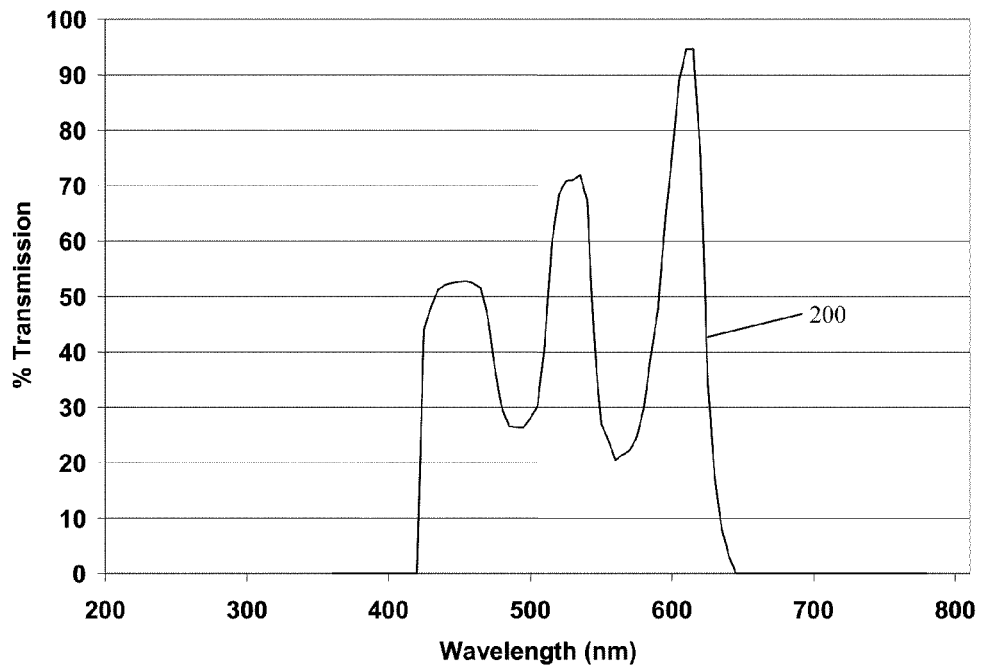
FIG. 5 depicts an example of a customized spectral profile.

By way of example, FIG. 5 illustrates a customized spectral profile 200 for a filter having a power transmission of about 43% (relative to the power transmission of a reference, in this case a Sylvania 58562 lamp, held at equivalent luminance) when optically coupled to an incandescent illuminant having a color temperature of about 3000K. Relative to a similar reference illuminant (3000K), customized spectral profile 200 has a color rendering using a modified CIE 13.3 method (including the DE00 color difference formula and Munsell 8 reflectance spectra) of about 94, and a lumens/watt efficiency of about 230%. While these numbers are seemingly excellent for a filter, and likely reduce photochemical damage as a whole when taken across the entire spectrum, customized spectral profile 200 is not CCS-neutral; instead, the peaks may increase hole burning and may pile-up excess light in wavelength regions in which one or more pigments may be relatively more susceptible to perceptible changes in appearance (e.g., changes in color).

Figure 6:
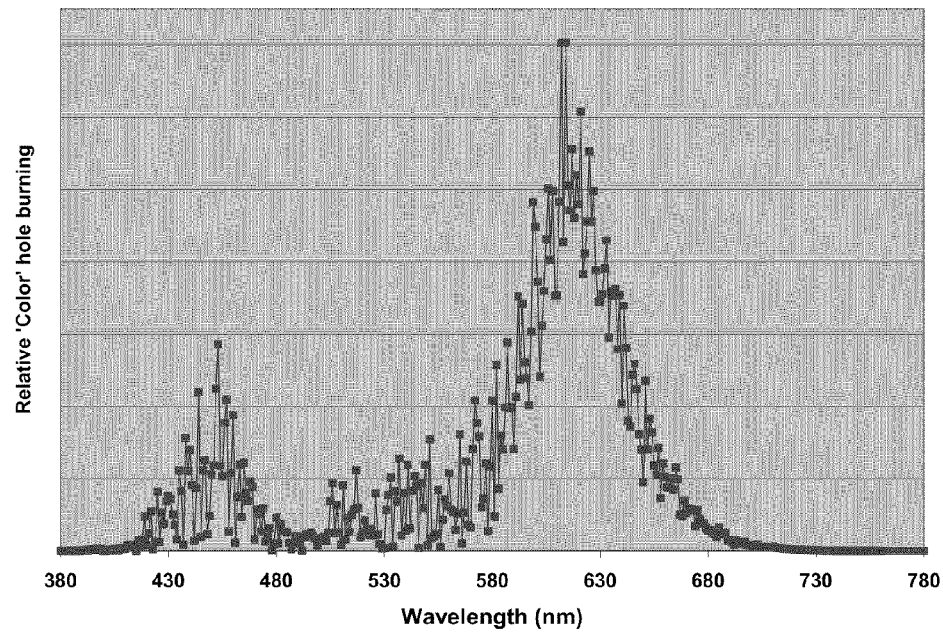
FIG. 6 depicts relative hole burning power of the customized spectral profile of FIG. 5 relative to a CCS-neutral filter.
Figure 7:
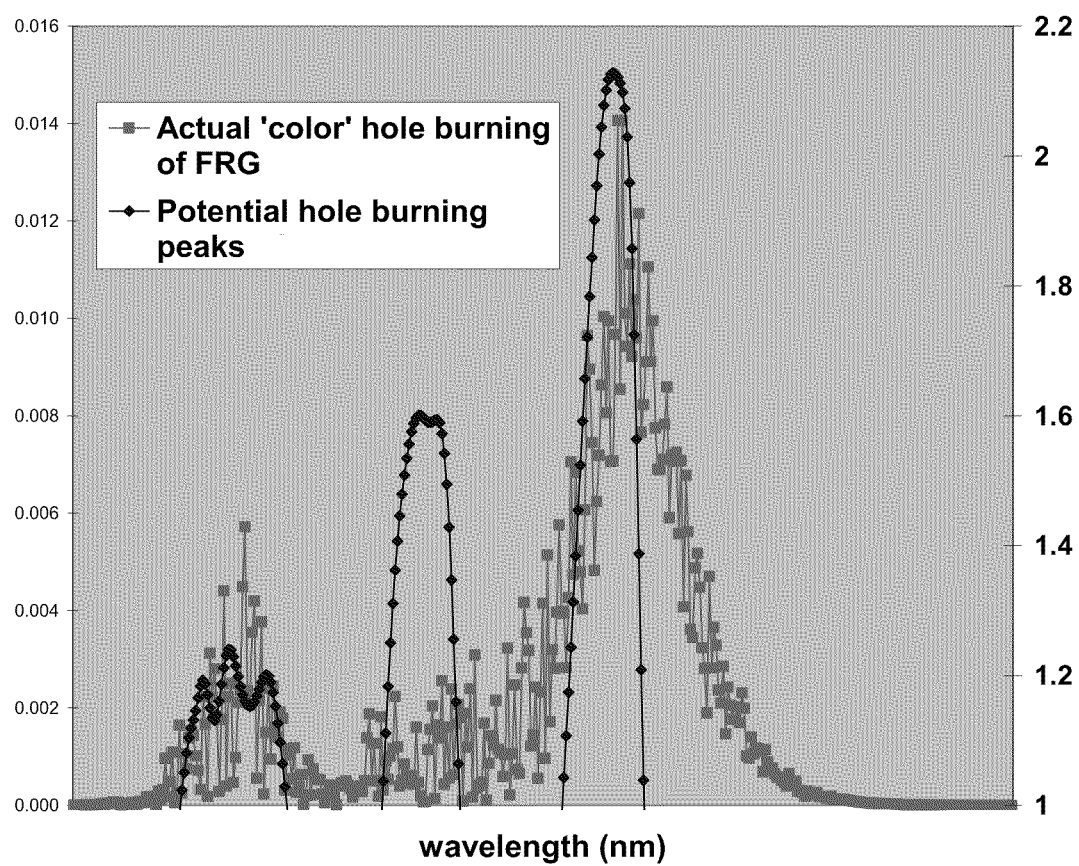
FIG. 7 depicts wavelength regions of the FRG pigment and the potential hole-burning peaks of the customized spectral profile of FIG. 5.

FIG. 6 illustrates a comparison of customized spectral profile 200 to a CCS-neutral filter that does not pile-up or permit excess light in only certain wavelength regions. More particularly, the curve of FIG. 6 illustrates the relatively greater potential of customized spectral profile 200 to cause hole burning in certain wavelength regions for flame red gauche (FRG) pigment, and thus the relatively greater potential to cause perceptible changes in appearance (e.g., color) of FRG pigment. Accordingly, FIG. 7 illustrates the three transmission peaks in customized spectral profile 200 with the wavelength regions of FRG pigment that are most susceptible to hole burning (and likely perceptible changes in color). As shown, the peaks of customized spectral profile 200 align with these more-susceptible regions, and even though customized spectral profile 200 is seemingly very good at protecting from photochemical damage across the spectrum, it may actually permit or even encourage photochemical damage that causes more-perceptible damage to the pigment. As such, the present methods may in some embodiments not reduce light in wavelength regions causing photochemical damage if that photochemical damage is not perceptible or is less perceptible.

In some embodiments, especially those utilizing the methods described in the Dirk patent applications incorporated by reference above, the step of optimizing further comprises optimizing the custom spectral profile such that an illuminant or filter configured to have the customized spectral profile will also have a color rendering index (CRI) of at least 85 (e.g., at least 90, at least 95, or the like) for the one or more pigments relative to an unfiltered reference illuminant (e.g., an incandescent illuminant having color temperature of about 3000K).

Figure 8:
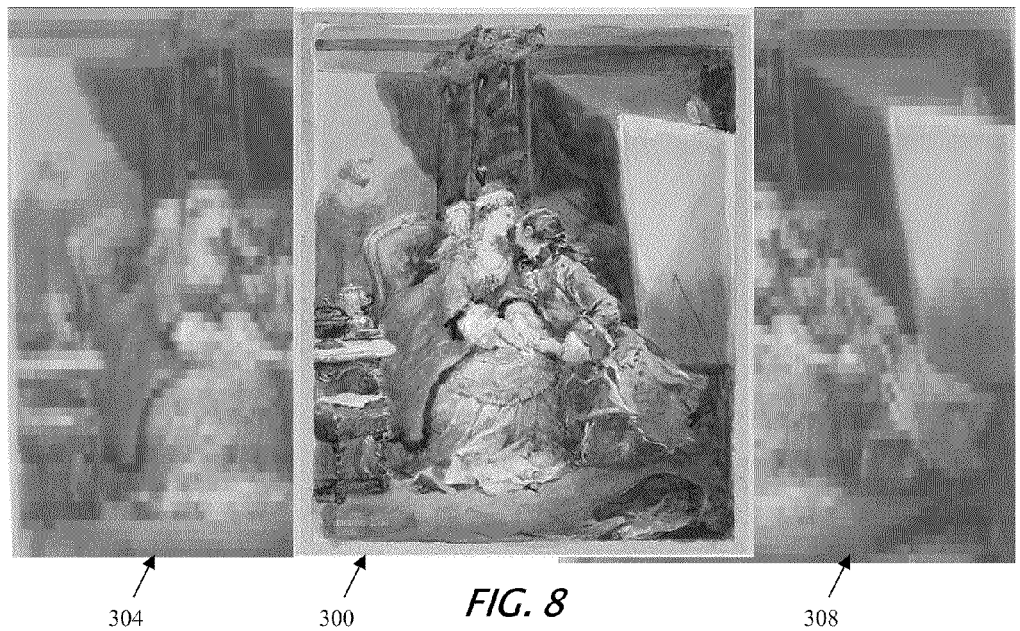
FIG. 8 depicts an image of a painting, and calculated image calculated from reflection spectral information of the painting for unfiltered illumination, and calculated image calculated from reflection spectral information of the painting for filtered illumination.
Figure 9:
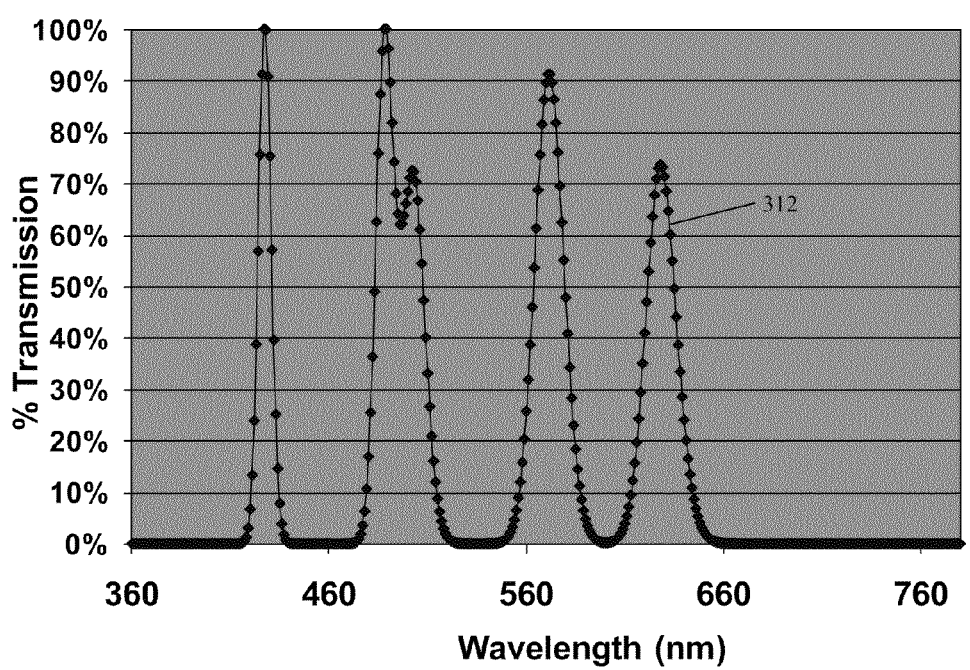
FIG. 9 depicts a customized spectral profile that has been optimized to reduce light in wavelength regions for which the painting of FIG. 8 is relatively more susceptible to perceptible changes in appearance.

In contrast, and with reference to FIGS. 8 and 9, a customized spectral profile can be optimized to maintain acceptable color rendering (e.g., 85 or above, 90 or above, 95 or above) while reducing light in more-susceptible (to perceptible changes in appearance) wavelength regions. FIG. 8 illustrates an image 300 of "A Couple Embracing in an Artist's Studio" (painted in 1881 by Eugène Louis Lami) along with a calculated image 304 under unfiltered 3000K incandescent illumination, and a calculated image 308 under filtered 3000K incandescent illumination, both calculated images derived from reflection spectral data of the artwork and the use of color theory to simulate how the image would appear at each pixel. Image 308 is modeled using Sylvania 58562 (though other 3000K color temperature incandescent lamp data would work as well) spectral emission data illuminant and a theoretical filter having customized spectral profile 312 shown in FIG. 9. As shown in FIG. 9, customized spectral profile 312 has an unusual shape for a filter spectrum. However, using calculated unfiltered image 304, or only data from selected pixels, customized spectral profile 312 has been optimized to reduce light in wavelength regions for which the painting shown in image 300 (e.g., the pigments of the painting) is relatively more susceptible to perceptible changes in color, even though at the wavelengths of the transmission maxima of customized spectral profile 312, the painting may be subject to photochemical damages of relatively greater magnitude than it would be in the transmission minima of customized spectral profile 312.

Some embodiments of the present methods further comprise coupling one or more filter layers to a substrate such that the substrate and filter layers are configured to have the customized spectral profile. For example, one or more first filter layers having a relatively higher index of refraction and one or more second filter layers having a relatively lower index of refraction can be coupled (e.g., in a stacked, alternating configuration) to a substrate such as glass such that the substrate and filter layers are configured to have the customized spectral profile (e.g., will filter light from an illuminant according to the customized spectral profile). Some embodiments of the present methods further comprise coupling one or more filter layers to an illuminant such that, if the illuminant is energized, the filter layers are configured to filter light from the illuminant according to the customized spectral profile.

Some embodiments of the present apparatuses comprise: an illuminant configured to emit light if the illuminant is energized; a plurality of filter layers coupled to the illuminant; where the apparatus is configured such that, if the illuminant is energized and emits light, the filter layers will: (a) block a portion of the light having wavelengths in one or more selected wavelength regions in which one or more pigments are relatively more susceptible to damage causing perceptible changes in appearance, and (b) transmit a portion of the light such that the transmitted light has a color rendering index of at least 85 for the one or more pigments relative to the illuminant without filter layers. For example, in FIG. 1, filter 42 can comprise a plurality of such filter layers and the filter layers (e.g., with a substrate) can be configured to filter light 34 from illuminant 38 in this manner. In some embodiments, the filter layers (e.g., filter 42) can be physically coupled to the illuminant (e.g., illuminant 38), such as, for example, by way of a frame or the like (not shown) that holds the filter in fixed relation to the illuminant. In some embodiments, one or more of the filter layers can be (e.g., coupled) in direct contact with the illuminant, such as, for example, where one or more filter layers are directly connected to the illuminant.

Filter layers can be coupled to a substrate, to one another, and/or to an illuminant by any suitable methods or processes, such as, for example, magnetron sputtering techniques (e.g., with a Leybold HELIOS coater, available from Leybold Optics, Alzenau, Germany, and possibly also available from Leybold Optics USA, Cary, N.C., U.S.A.).

CCS, for example, may be important in the design and use of LED illuminants for Museum lighting. Typical three-color light-emitting diode (LED) illuminants have lighting devices tuned to the wavelengths of the maxima of the cone cells in human vision. This is one way to ensure good color rendering. However, CCS results suggest that this will preferentially place light in regions that can cause the highest color changes with relatively small photochemical changes. Thus, the typical three color LED illuminants may specifically not be suitable for many museum lighting applications. One can design an LED illuminant to minimize and neutralize the CCS effect, such as, for example, with 4, 5. 6, or more LEDs with different spectral emissions arranged to minimize the impact on CCS, but to maximize color rendering. In some instances, a three-color LED could be retuned to both inhibit color change and retain reasonable color rendering, such as, for example, by using LEDs with spectral emissions at least partially (up to mostly and/or entirely) outside the peaks of sensitivity for cones in human eyes.

The various illustrative embodiments of devices, systems, and methods described herein are not intended to be limited to the particular forms disclosed. Rather, they include all modifications, equivalents, and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

The invention claimed is:

1. A method of generating a customized spectral profile, the method comprising:
   determining for one or more pigments one or more wavelength regions for which the one or more pigments are relatively more susceptible to perceptible changes in color than for one or more other less-susceptible wavelength regions;
   optimizing a spectral profile to generate a customized spectral profile such that an illuminant or filter configured to have the customized spectral profile will reduce light in the one or more more-susceptible wavelength regions.

2. The method of claim 1, where optimizing further includes optimizing the spectral profile to generate a customized spectral profile such that an illuminant or filter configured to have the customized spectral profile will reduce light to a lesser degree in the one or more less-susceptible wavelength regions than in the one or more more-susceptible wavelength regions.

3. The method of claim 2, where at least one less-susceptible wavelength region is less susceptible to photochemical damage than at least one more-susceptible wavelength region.

4. The method of claim 1, where the step of optimizing further comprises optimizing the custom spectral profile such that an illuminant or filter configured to have the customized spectral profile will also have a color rendering index (CRI) of at least 85 for the one or more pigments relative to an unfiltered reference illuminant.

5. The method of claim 4, where the step of optimizing further comprises optimizing the custom spectral profile such that an illuminant or filter configured to have the customized spectral profile will also have a color rendering index (CRI) of at least 90 for the one or more pigments relative to an unfiltered reference illuminant.

6. The method of claim 5, where the step of optimizing further comprises optimizing the custom spectral profile such that that an illuminant or filter configured to have the customized spectral profile will also have a color rendering index (CRI) of at least 95 for the one or more pigments relative to an unfiltered reference illuminant.

7. The method of claim 4, where the unfiltered reference illuminant is an incandescent lamp having a color temperature of about 3000K.

8. The method of claim 1, where the step of determining comprises:
   obtaining a reflection spectrum for the one or more pigments; and
   determining color change susceptibility (CCS) of the one or more pigments across the reflection spectrum.

9. The method of claim 8, where the step of optimizing comprises:
   identifying one or more peaks or shoulders of CCS across the reflection spectrum for the one or more pigments, the peaks or shoulders each corresponding to a wavelength region in which the pigment is relatively more susceptible to damage causing perceptible changes in appearance; and
   modifying the customized spectral profile to reduce light in the one or more wavelength regions.

10. The method of claim 8, where the step of determining CCS comprises calculating a color change or change in color rendering per unit change in reflectance across the reflection spectrum for the pigment.

11. The method of claim 8, where the step of obtaining a reflection spectrum comprises imaging the reflection spectrum with a spectral imaging camera or other spectral imaging device controlled by suitably programmed software.

12. The method of claim 1, where the step of determining comprises determining two or more wavelength regions in which the one or more pigments are relatively more susceptible to damage causing perceptible changes in appearance, and where modifying comprises modifying the customized spectral profile to reduce light in each of the two or more wavelength regions.

13. The method of claim 12, further comprising:
   coupling one or more filter layers to a substrate such that the substrate and filter layers are configured to have the customized spectral profile.

14. The method of claim 12, further comprising:
   coupling one or more filter layers to an illuminant such that, if the illuminant is energized, the filter layers are configured to filter light from the illuminant according to the customized spectral profile.

15. A method of generating a customized spectral profile, the method comprising:
   determining for an image a plurality of wavelength regions in which one or more pigments of the image are relatively more susceptible to damage causing perceptible changes in appearance;
   optimizing a custom spectral profile for a filter or illuminant to reduce light in each of the wavelength regions.

16. An apparatus comprising:
   an illuminant configured to emit light if the illuminant is energized;
   a plurality of filter layers coupled to the illuminant;
   where the apparatus is configured such that, if the illuminant is energized and emits light, the filter layers will:
      (a) block a portion of the light having wavelengths in one or more selected wavelength regions in which one or more pigments are relatively more susceptible to damage causing perceptible changes in appearance, and
      (b) transmit a portion of the light such that the transmitted light has a color rendering index of at least 85 for the one or more pigments relative to the illuminant without filter layers.

17. The apparatus of claim 16, where the filter layers are physically coupled to the illuminant.

18. The apparatus of claim 17, where one or more of the filter layers are in direct contact with the illuminant.

* * * * *

UNITED STATES PATENT AND TRADEMARK OFFICE
CERTIFICATE OF CORRECTION

| | | |
|---|---|---|
| PATENT NO. | : 8,570,498 B2 | Page 1 of 1 |
| APPLICATION NO. | : 12/780546 | |
| DATED | : October 29, 2013 | |
| INVENTOR(S) | : Carl W. Dirk | |

It is certified that error appears in the above-identified patent and that said Letters Patent is hereby corrected as shown below:

In the Claims
In claim 6 on column 13, line 41, remove "that".

Signed and Sealed this
Fourteenth Day of January, 2014

Michelle K. Lee
*Deputy Director of the United States Patent and Trademark Office*